(12) United States Patent
Buettner et al.

(10) Patent No.: US 8,597,579 B1
(45) Date of Patent: Dec. 3, 2013

(54) MOLECULARLY IMPRINTED POLYMER-DENUDER BASED SENSORS

(75) Inventors: Leonard C. Buettner, Catonsville, MD (US); Amanda L. Jenkens, Salisbury, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/010,383

(22) Filed: Jan. 20, 2011

Related U.S. Application Data

(60) Provisional application No. 61/307,099, filed on Feb. 23, 2010.

(51) Int. Cl.
*G01N 15/06* (2006.01)
*G01N 33/00* (2006.01)
*G01N 33/48* (2006.01)

(52) U.S. Cl.
USPC .................. 422/83; 422/50; 422/88; 422/93; 422/98; 436/43

(58) Field of Classification Search
USPC ........................ 422/50, 83, 88, 93, 98; 436/43
See application file for complete search history.

*Primary Examiner* — Brian J Sines
(74) *Attorney, Agent, or Firm* — Ulysses John Biffoni

(57) ABSTRACT

A molecularly imprinted polymer denuder sensor that includes a trapping solution; a delivery device transporting the trapping solution; a denuder operatively connected to the trapping solution and contacting ambient air, wherein the denuder infuses the sample into the trapping solution; a molecularly imprinted polymer sensor operatively connected to the denuder, wherein the MIP sensor captures and detects the threat material; an excitation source operatively connected to the MIP sensor and having an excitation band, wherein the excitation band excites europium (or other signal transducing lanthanide or metal ion) in the MIP when it is bound to the threat material providing unique emission band(s); and an analytical device operatively connected to the MIP sensor, wherein the analytical device senses the presence of the threat material in the sample.

14 Claims, 4 Drawing Sheets

MOLECULARLY IMPRINTED POLYMER-DENUDER BASED SENSORS

RELATED APPLICATION

This application claims the benefit of priority from U.S. provisional application Ser. No. 61/307,099 filed on Feb. 23, 2010.

GOVERNMENT INTEREST

The embodiments herein may be manufactured, used, and/or licensed by or for the United States Government.

BACKGROUND

1. Technical Field

The embodiments herein generally relate to sensing methods and devices, and more particularly, to sensing solutions, gases, aerosols, and vapors.

2. Description of the Related Art

Nano-materials and detector platforms capable of capturing and detecting agents of chemical and biological significance in a variety of environments are desperately needed. Conventional approaches to this problem use a combination of micro-organisms, enzymes, and antibodies for the molecular recognition of chemical compounds. All of these assays, however, require an additional tagging step for signal transduction, making real-time sensing very difficult. In addition, bio-receptor (e.g., antibodies) technologies typically suffer shelf-stability problems, are generally not reversible (i.e., one time use), and are frequently limited in their capacity for small molecule recognition. Furthermore, non-biologically based detection technologies (e.g., ion mobility spectrometry), typically suffer from sensitivity problems and "false positive" results. Still other instrument-based detector technologies either require complicated algorithms to get meaningful data or their size, weight, and logistics prohibit their use in restrictive environments (e.g., a battlefield). Moreover, current sensing systems are generally not capable of aerosol, liquid and vapor analysis on the same platform in real time.

Therefore for the reasons stated above, and for other reasons stated below which will become apparent to those skilled in the art upon reading and understanding the present specification, there is a need in the art for an alternative sensing platform for detecting chemical and biological agent solutions, aerosols, and vapors.

SUMMARY

In view of the foregoing, an embodiment herein provides a system for sensing an air or solution borne threat material within a sample of ambient air or solution, the system comprising a trapping solution; a delivery device transporting the trapping solution; a denuder in contact with the trapping solution and contacting ambient air, wherein the denuder infuses the sample into the trapping solution; a molecularly imprinted polymer (MIP) sensor operatively connected to the denuder, wherein the MIP sensor captures and detects the threat material; an excitation source operatively connected to the MIP sensor and having an excitation band, wherein the excitation band excites the threat material providing unique emission band(s); and an analytic device operatively connected to the MIP sensor, wherein the analytic device senses the presence of the threat material in the sample.

In such a system, the excitation source may comprise any of an ion laser, solid state laser, diode laser, tunable laser, pen light and or light emitting diode. Furthermore, the MIP sensor may comprise at least one of an optical fiber, a well plate, a mirror, a cuvette, and any other substrate/platform having disposed thereon a molecularly imprinted polymer chemically binding to the threat material. This molecularly imprinted polymer comprises a lanthanide-complex doped into a polymer, which is then affixed to any of the foregoing substrates or platforms. Moreover, the lanthanide-complex may comprise a lanthanide ion derived from a lanthanide comprising any of lanthanum, cerium, praseodymium, neodymium, promethium, samarium, europium, gadolinium, terbium, dysprosium, holmium, erbium, thulium, ytterbium, and lutetium. In addition, the lanthanide ion may comprise any of a europium ion and a terbium ion. Furthermore, the lanthanide ion may comprise a +3 europium ion. Additionally, the lanthanide ion may be chelated with a polymerized derivate of one or more ligands comprising any of 4-vinyl benzoic acid, methyl-3,5-divinyl benzoate, 4-vinyl-2-hydroxybenzaldehyde oxime, 2-hydroxy-1,2-di-4-vinylphenylethanone or other vinyl substituted ligand.

In such a system the analytic device may also comprise any of a spectrophotometer, spectrometer, photomultiplier tube, monochromator equipped with a charge-coupled device (CCD) camera, filters, the naked eye, a computing device, and combinations thereof. Such a system may further comprise at least one of a stream selector valve, a series of on/off solution valves and switches, and a solenoid valve operatively connected to the delivery device; and at least one standard solution, wherein the standard solution and the trapping solution are operatively transported through at least one of the stream selector valve, the series of on/off solution valves and switches, and the solenoid to the delivery device. In addition, such a system may further comprise a collection container operatively connected to the MIP sensor and the denuder; and a liquid waste container operatively connected to the collection container.

Moreover, such a system may further comprise an airflow control device operatively connected to the liquid waste container; and a vacuum source operatively connected to the airflow control device. In addition, the airflow control device may comprise at least one of a mass flow controller, limiting orifice, and a rotometer, etc. Furthermore, the threat material may comprise at least one of a liquid gas and aerosol of at least one of an organophosphorus and other target chemical of interest. Additionally, the delivery device may comprise at least one of a solenoid, syringe, peristaltic, rotary, high performance liquid chromatography (HPLC) and other liquid pump.

Embodiments herein also provide an apparatus for capturing a threat material within a sample of ambient air, the system comprising at least one of a stream a selector valve, a series of on/off solution valves and switches, and a solenoid; a delivery device operatively connected to the stream selector valve; a trapping solution; at least one standard solution, wherein at least one of the standard solution and the trapping solution are operatively transported through at least one of the solution selector valve, the series of on/off solution valves and switches, and the solenoid to the delivery device; a denuder in contact with the trapping solution and exposed to the sample of ambient air, wherein the denuder infuses the sample of ambient air into the trapping solution; and a molecularly imprinted polymer (MIP) device operatively connected to the denuder, wherein the MIP sensor captures the threat material.

In such an apparatus, the MIP device may comprise a MIP-coated optical fiber. Moreover, the MIP device may comprise a MIP-coated lens. Furthermore, the MIP device may comprise a well plate reader comprising a plurality of wells of MIPs. Additionally, each well in the well plate reader may comprise a MIP-coated substrate.

Embodiments herein further provide a system for detecting a target chemical of interest within an ambient air or solution based sample, the system comprising a trapping solution; a delivery device transporting the trapping solution; a denuder in contact with the trapping solution and probing the ambient air sample, wherein the denuder infuses the ambient air sample into the trapping solution, and wherein the denuder comprises a probe housing; at least one optical fiber, lens, well plate or other substrate; a molecularly imprinted polymer (MIP) sensor operatively connected to the denuder, wherein the MIP sensor comprises a lanthanide-complex disposed on the distal end of the optical fiber, wherein the lanthanide-complex chemically binds with the target compound; a light source for generating excitation energy, wherein the light source is operatively connected to the at least one optical fiber to allow the excitation energy to pass through the optical fiber; a collection container operatively connected to the MIP sensor and the denuder; a liquid waste container operatively connected to the collection container; an airflow control device operatively connected to the liquid waste container; a vacuum source operatively connected to the airflow control device; and an analytic device operatively connected to the MIP sensor, wherein the analytic device senses the presence of a solution or airborne imprinted threat material in the ambient air or solution sample.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
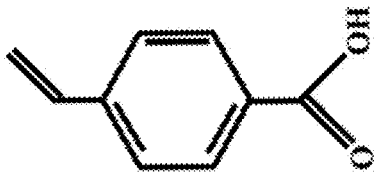
FIGS. 1A through 1D illustrate example structural representations of monomers according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an apparatus and method of sensing chemical agents in gases, aerosols and solutions. For example, in one embodiment described herein, a denuder is designed to take a gas, vapor, or aerosol sample and, using an appropriate trapping solution, extract the analyte into a mobile phase. The trapping solution comprises a solvent system appropriate for the target sample based on the solubility of the target compound. Therefore, selection of an appropriate trapping solution will depend on the target compound of interest and will be well known of those of ordinary skill in the art. A molecularly imprinted polymer ("MIP") sensor is coupled to the denuder and senses that a target material has been captured and transferred into solution with great efficiency (e.g., greater than 95%). Referring now to the drawings, and more particularly to FIGS. 1 through 4, where similar reference characters denote corresponding features consistently throughout the figures, there are shown preferred embodiments.

The embodiments discussed below describe non-limiting techniques of molecularly imprinting and sensitized lanthanide luminescence, thereby providing multiple criteria for selectivity for an analyte and virtually eliminating the possibility for false positive readings. The lanthanide elements, also known as the rare earth elements, consist of the elements having atomic numbers from 57 to 71. As used herein, the term "lanthanide" refers to the following elements of the periodic table: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In the embodiments described below, a lanthanide is chosen as the transducer for a sensor/detector device because the trivalent lanthanide ions have excellent spectroscopic properties such as long luminescence lifetimes and narrow bandwidths, usually only a few nanometers. Preferred lanthanide ions that exhibit a narrow-line luminescence include the +3 ions of samarium, europium, dysprosium, terbium, and neodymium, with europium and terbium being most preferred.

Molecularly imprinted polymers (MIPs) are synthetic, regenerable nano-materials that mimic the function of biological receptors such as enzymes and exhibit virtually no stability constraints. As used herein, the terms "molecularly imprinted molecule," "molecularly imprinted polymer", and "MIP" refer to a molecular antibody-like structure that has pre-organized interactive moieties complementing the spacing of binding sites on a template or template molecule. The interactive moieties can be, for example, chemical groups or affinity ligands. The geometrical organization of interactive moieties imparts selective binding characteristics for the template substance onto the imprinted polymer. The term "selective binding interactions" is intended to refer to preferential and reversible binding exhibited by an imprinted polymer for its template molecule (e.g., organophosphorus compound) compared to other non-template molecules. Selective binding includes both affinity and specificity of the imprinted polymer for its template molecule.

In the embodiments described below, molecular imprinting creates specific recognition sites in materials, such as polymeric organic materials. For example, in one embodiment, the molecular imprinting occurs via cross-linking materials in the presence of a functional monomer or mixture of monomers. In such an embodiment, the template molecule interacts with a complementary portion of a functional monomer, either covalently or by other interactions such as ionic, hydrophobic or hydrogen bonding, so that recognition sites for the template molecule can be provided in the substrate material. The template molecule is subsequently removed from the substrate to leave a "cavity" or recognition site. Thus, a non-specific molecule can be shaped to the contours of a specific target, and when the target is removed, the shape is maintained to give the synthetic antibody a propensity to rebind the target. This process is known as "molecular imprinting" or "templating".

The target or template molecule directs the positioning of the encapsulating antibody by the interactions that occur between certain sites on the target and complementary sites on the antibody. The sites that allow complementary associations are certain arrangements of atoms that exhibit an electrostatic attraction of a specific kind. These localized atomic arrangements are sometimes referred to as "functional groups". The functional groups on a molecule help to define the molecule's overall chemical properties. In the embodiments described below, the MIP exhibit as closely as possible the reverse topology of the template molecule, similar to a lock and key type mechanism. The synthetic production of polymers with selective binding for a specific molecule is achieved by providing polymers with cavities lined with complexing groups or "ligands" arranged to match the charge, coordination number, coordination geometry, and size of the target molecule. Ionic complexing polymers are made in a similar manner, but typically employ a trapped metal ion that has a large affinity for the target in question. These cavity containing polymers are produced by using a specific ion as a template around which monomeric complexing ligands will be self-assembled and later polymerized. The complexing ligands are ones containing functional groups known to form stable complexes with the specific ion and less stable complexes with other ions.

For example, embodiments described below include MIPs created for the detection of both hydrolyzed and non-hydrolyzed organophosphonate compounds. In such embodiments, the MIPs may include the polymerization of mono- and di-functional vinyl monomers in the presence of an analyte, followed by the release of the analyte through a simple washing process to generate a binding receptor that is specific for the imprinted analyte. The recognition mechanism is based on the size, shape, and chemical functionality of the analyte, very similar to that of antibody-antigen binding reactions, but without the need for fluorescence tags to do signal transduction. This is because, upon binding with the lanthanide metal ion, organophosphonate based compounds (i.e. nerve agents, pesticides/insecticides, and their hydrolyzed products) produce a unique spectral signatures (e.g., in the 600-700 nm region of the lanthanide spectra). Thus, adding luminescent components to these polymers also provides enhanced chemical affinity for the analyte of interest.

One step in making a molecularly imprinted polymer is to form a complex that will survive the polymerization process and leave behind a suitable set of binding sites when the templating species is removed. To form such a complex, ligands must be chosen that exhibit sufficiently large affinities to resist dissociation. The success of the end product hinges on the selection of the ligating monomer. In addition, the polymerization process must provide sufficient rigidity to effect structural "memory" but be sufficiently flexible to allow removal of the template ion.

Figure 1B:
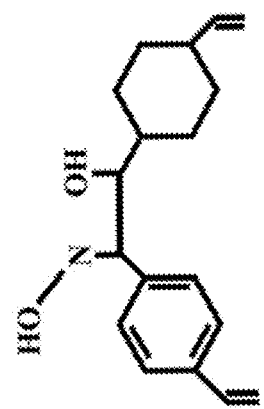
Figure 1C:
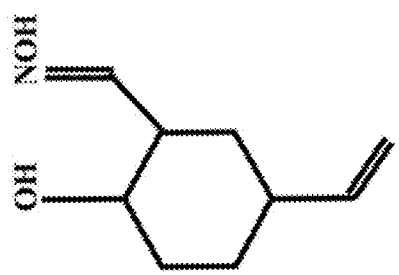
Figure 1D:
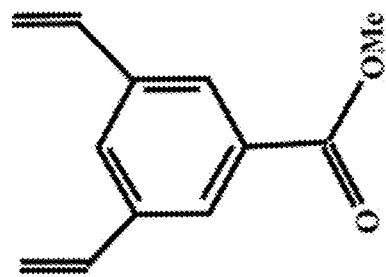

Any suitable monomer that provides an accurate imprint of the template molecule on polymerization may be used for the synthesizing a MIP in accordance with the principles described above. For example, chemical representations of preferred monomers are shown in FIGS. 1A through 1D. For example, FIG. 1A illustrates 4-vinyl benzoic acid; FIG. 1B illustrates 2-hydroxy-1,2-di-4-vinylphenylethanone (benzoin oxime vinyl derivative); FIG. 1C illustrates 4-vinyl-2-hydroxybenzaldehyde oxime (vinylsalicylaldoxime); and FIG. 1D illustrates methyl-3,5-divinyl benzoate (MDVB).

Further suitable non-limiting examples of monomers that can be used for preparing a MIP of the embodiments herein include: methylmethacrylate, other alkyl methacrylates, alkylacrylates, ally or aryl acrylates and methacrylates, cyanoacrylate, styrene, methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 50 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; N-acryloxy succinimide N-acryloxytris(hydroxymethyl)aminomethane; N-acryloly chloride; N-acryloyl pyrrolidinone; N-acryloyl-tris(hydroxymethyl) amino methane; 2-amino ethyl methacrylate; N-(3-aminopropyl)methacrylamide; (o,m,p)-aminostyrene; t-amyl methacrylate; 2-(1-aziridinyl)ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4-dimethylvaleronitrile); 4-benzyloxy-3-methoxystyrene; 2-bromoacrylic acid; 4-bromo-1-butene; 3-bromo-3,3-difluoro-propane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; β-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (−)-carvyl acetate; c is 3-chloro-acrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dim-ethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylethyl styrene; 3,4-dimethylstyrene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride; 1-dodecene; 3,4-eoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl) tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,1-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene iso-cyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy)ethyl trimethyl ammonium methylsulfate; 2-methoxy propene (isopropenylmethyl ether); methyl-2-(bromomethyl)acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-17 pentene; 2-(bromomethyl)acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (–)-carvyl acetate; c is 3-chloroacrylic acid; 2-chloroacrylonitrile; 2-chloroethyl vinyl ether; 2-chloromethyl-3-trimethylsilyl-1-propene; 3-chlorobutene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (–)-dihydrocarvyl acetate; 3,3-diethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstyrene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride; 1-dodecene; 3,4-eoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl) tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexa-dien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,1-dodecatriene; isoamyl methacrylate; isobutyl methacrylate; isoprene; 2-iso-propenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-17 pentene; α-methyl styrene; t-a-methylstyrene; t-β-methyl-styrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t-β-nitro styrene; 3-nitrostyrene; 1-nonadecene; 1,8-nonadiene; 1-octadecene; 1,7-octadiene; 7-octene-1,2-diol; 1-octene; 1-octen-3-01; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfo-propyl methacrylate sodium salt; tetrachloroethylene; tetracyano ethylene; tetramethyldivinyl siloxane; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyllaurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl tri-acetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl-vinyl phosphonium bromide); vinyl tris-(2-meth-oxyethoxy)silane; vinyl 2-valerate and the like.

Acrylate-terminated or otherwise unsaturated urethanes, carbonates, and epoxies can also be used in the MIP. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Cross-linking agents that lend rigidity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene)tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy: L-2-isocyanatoethyl methacrylate, 1,1-dimethyl-2-isocyanatoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

Embodiments herein use any ratio of simple monomers to cross-linking monomers that provides a structure of appropriate integrity. Those skilled in the art can select suitable ratios of monomers to provide the desired structural integrity. While free radical polymerization is preferred, monomers can also be selected that are polymerized cationically or anionically. Embodiments herein select polymerization conditions that do not adversely affect the template molecule. Any UV or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile (AIBN), t-butyl peracetate, cumyl peroxide, t-butyl peroxide, t-butyl hydroperoxide, bis(isopropyl) peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenyl-acetophenone, and phenothiazine and diisopropylxanthogen disulfide. Consequently, when the polymerization is complete, the cross-linked polymer may be washed, cryogenically ground to a uniformly fine powder, and extensively eluted with non-polar solvents to remove unreacted complex. Some embodiments herein use the steps of grinding and/or freezing in liquid nitrogen to maximize surface area and allow for access by the various reagents and samples. Freezing allows the polymer to become sufficiently brittle to be ground and prevents distortions of the polymer by the heat of friction. Moreover, polymers used in the construction of optical sensors may be prepared in situ on the distal end of an optical fiber whose surface is coated by binding an imprinted polymer on the surface or by coating the MIP onto well plates, cuvettes, or other substrates.

Figure 2:
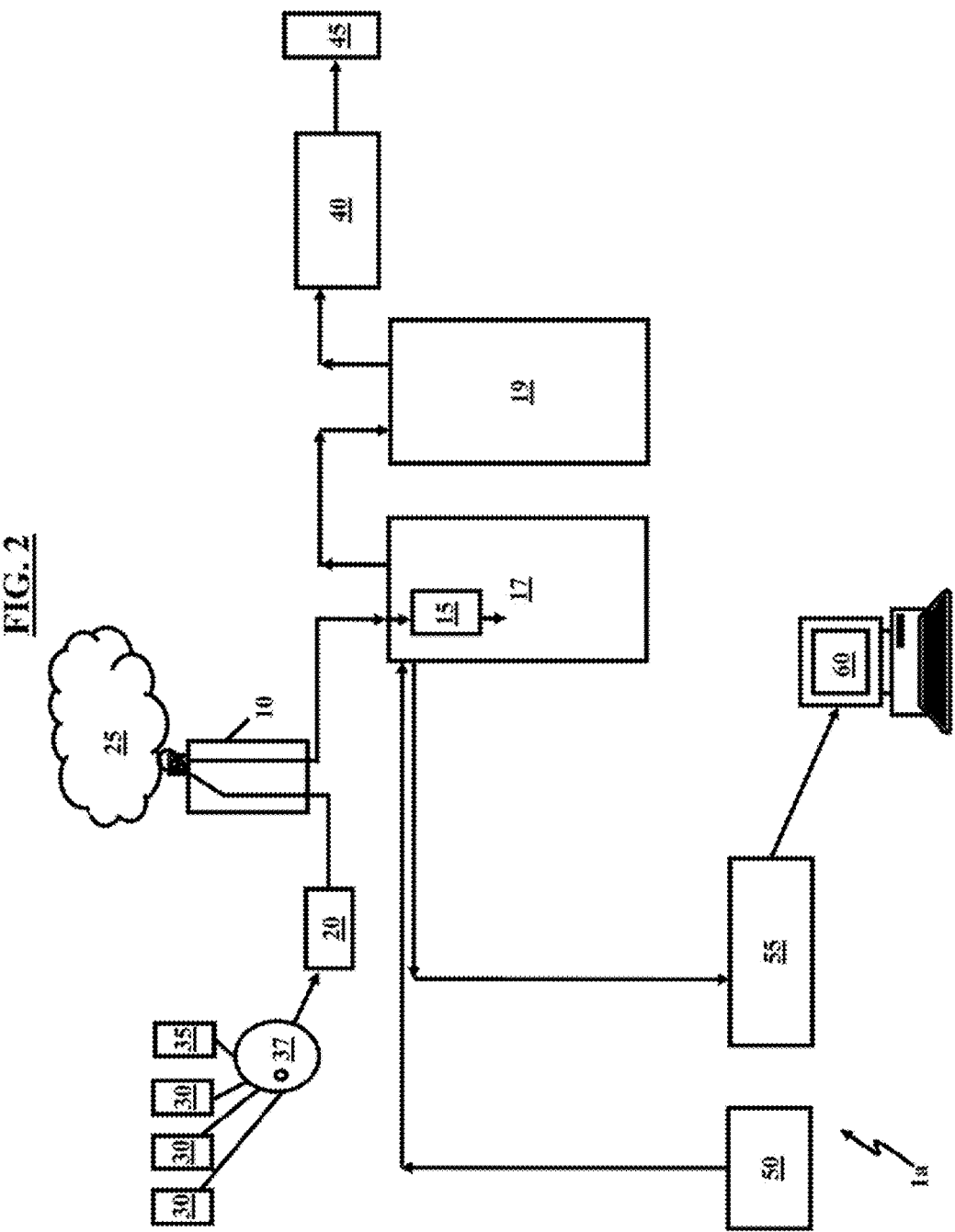
FIG. 2 illustrates a schematic diagram of a detection system according to an embodiment herein.

FIG. 2, with reference to FIGS. 1A through 1D, illustrates a sensor according to an embodiment herein. Sensor 1a, as shown in FIG. 2, includes a denuder 10, a MIPs sensor 15, a liquid-vapor separating collection container 17, a liquid waste container 19, a liquid delivery device 20, threat material 25 (which may be taken from an air or liquid sample), standard solutions 30, a trapping solution 35, a stream selector valve 37, an airflow control device 40, a vacuum 45, an excitation source 50, an optional spectrometer 55, and an optional computing device 60. The standard solution 30 serves as a calibration standard and comprises the target sample in several different concentrations. According to one embodiment herein, denuder 10 includes a continuous impinger 12 (e.g., in a probe housing). Accordingly, denuder 10 uses gas injection analysis technology (e.g., flow injection analysis) to continuously introduce a gas or aerosol sample (e.g., threat material 25) into a solvent stream (e.g., standard solution 30 or trapping solution 35) where the analyte of interest (e.g., organophosphorus or other electron donating compound) is taken up into a trapping solution 35. Thereafter, the trapping solution 35 is delivered to denuder 10 at a predetermined rate (e.g., between 1-4 mL/min) using delivery device 20 (e.g., a solenoid-pump, syringe, peristaltic, rotary or high performance liquid chromatography pump (HPLC pump)). In addition, airflow is also introduced (e.g., 1-10 L/min) using an airflow control device 40 (e.g., a mass flow controller, rotometers, or critical orifice) and vacuum source 45. In the embodiment shown in FIG. 2, the airflow control device 40 is located external to an analytical device (e.g., spectrometer 55 and computing device 60) and draws sample air into denuder 10, where the chemical agent gases and aerosols (e.g., threat material 25) are immediately extracted into the liquid phase of trapping solution 35. In addition to the spectrometer 55 and computing device 60, alternative/additional analytical devices (not shown) may be used such as, a spectrophotometer, photomultiplier tube, monochromator equipped with a CCD camera, filters, and the naked eye. The resulting mixture is then immediately passed over the MIP sensor 15 (e.g., a molecularly imprinted polymer coated fiber or substrate) and sent to an analytical device (e.g., (e.g., spectrometer 55 and computing device 60). The trapping solution 35 can then be discarded or re-circulated (e.g., via liquid waste container 19) by an inline liquid pump and a solvent clean-up filter (not shown) to continue collection (e.g., via reintroduction to the pump 20) and provide a cumulative detection scheme that requires a minimal amount of solvent for operation.

In FIG. 2, detection is based on luminescence of the polymer typically excited at either 365 nm or 465.8 nm using excitation source 50 (e.g., an ion, solid state or diode laser, or light emitting diode (LED)). The resulting spectra are collected using a monochrometer with a direct fiber coupler and charge-coupled device (CCD) camera (not shown) or with a miniature fiber optic spectrometer (e.g., spectrometer 55) or other light detecting device. The intensity of the light emitted in the approximate 600-700 nm range of the spectra is directly proportional to the amount of analyte present.

While not shown in FIG. 2, an alternative embodiment of the MIPs sensor 15 comprises coating imprinted polymers (as described above) onto a lens system. By coating a lens system, greater coupling of threat material 25 and greater collection of light allows for more sensitivity, and provides more available sites for collection of threat material 25 to thereby allow higher concentrations to be detected in trapping solution 35.

Figure 3:
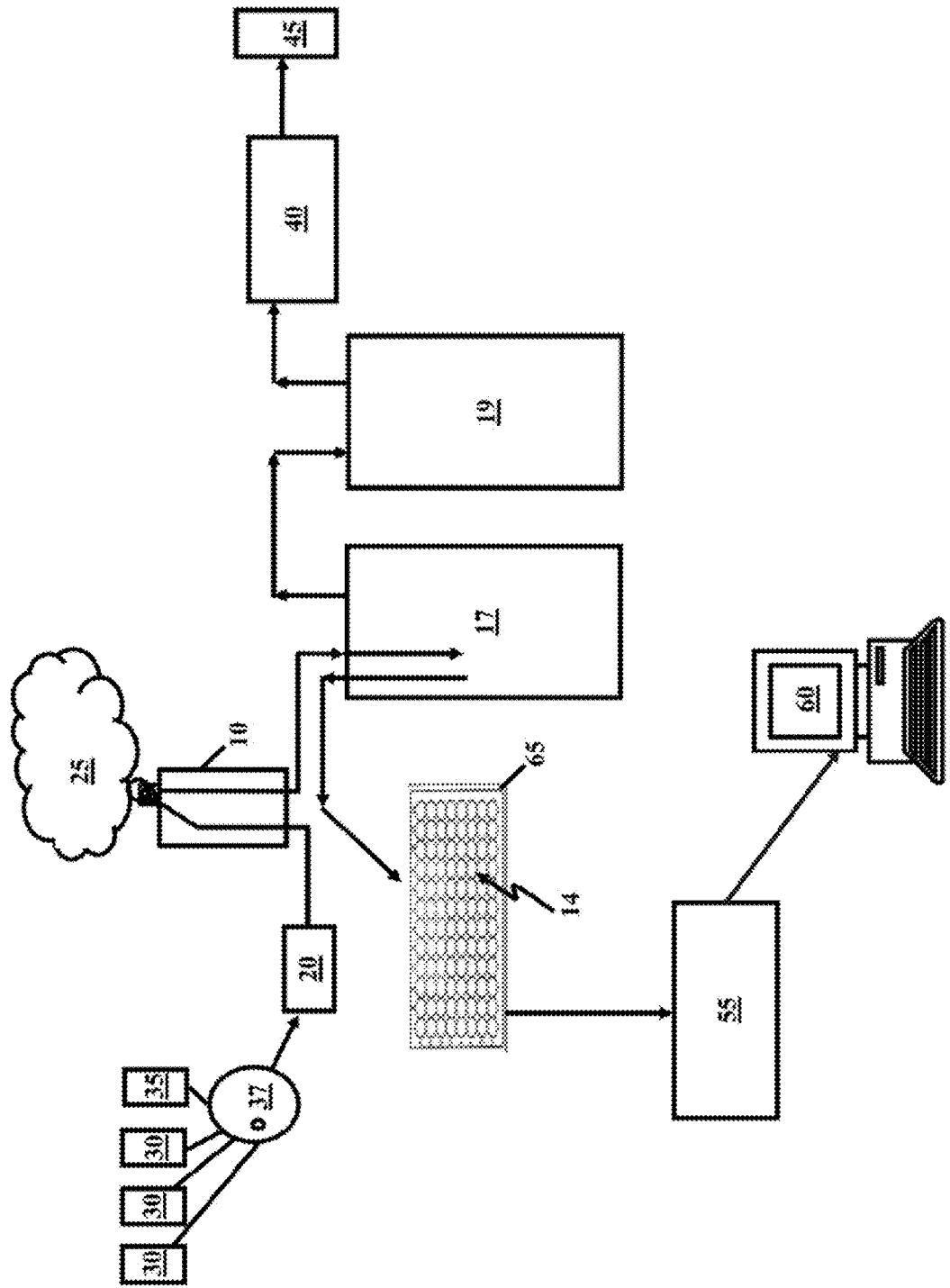
FIG. 3 illustrates a schematic diagram of an alternative detection system according to an embodiment herein.

FIG. 3, with reference to FIGS. 1A through 2, illustrates an alternative embodiment of sensor 1a, according to an embodiment herein. As shown in FIG. 3, sensor 1b includes a denuder 10, a delivery device 20, threat material 25 (which may be taken from an air or liquid sample), standard solutions 30, trapping solution 35, a stream selector valve 37, a MIP-coated well plate 65 and a fluorescence well plate reader 55. As shown in FIG. 3, the denuder 10 uses gas injection analysis technology (e.g., flow injection analysis) to continuously introduce a gas or aerosol sample (e.g., threat material 25) into a solvent stream (e.g., standard solution 30 or trapping solution 35) where the analyte of interest (e.g., organophosphorus or other target compound) is taken up into a trapping solution 35.

Thereafter, the trapping solution 35 is delivered to denuder 10 at a predetermined rate (e.g., between 1-4 mL/min) using delivery device 20 (e.g., a solenoid-pump, syringe, peristaltic, rotary or high performance liquid chromatography pump (HPLC pump)). In addition, airflow is also introduced (e.g., 1-10 L/min) using an airflow control device 40 (e.g., a mass flow controller, rotometers, or critical orifice) and vacuum source 45. In the embodiment shown in FIG. 3, the airflow control device 40 draws sample air into denuder 10, where the chemical agent gases and aerosols (e.g., threat material 25) are immediately extracted into the liquid phase of trapping solution 35. The resulting mixture is then pulled into a collection vessel 17 where it is transported to and immediately passed over the MIP coated well plate 65 which is read by an analytical device (e.g., fluorescence well plate reader 55 and computing device 60). In addition to the well plate reader 55 and computing device 60, alternative/additional analytical devices (not shown) may be used such as, a spectrophotometer, photomultiplier tube, monochromator equipped with a CCD camera, filters, and the naked eye. A waste collection bottle 19 prevents solution from being drawn into the airflow control device 40. According to the embodiment of FIG. 3, a series of MIPs wells 14 are used in a fluorescence well plate 65 and the fluorescence well plate reader 55 is used to detect a variety of compounds instead of a single MIPs sensor (e.g., MIPs sensor 15, shown in FIG. 2) for single compound detection. Thus, according to the embodiment shown in FIG. 3, each well (e.g., in a 98 or 256 well device) is coated with a polymer imprinted for a different target. In this way, the effluent could be evaluated for many different analytes at the same time.

The embodiments herein provide for the ability to detect liquids, aerosols and gases phase analytes. For example, the embodiments described herein may be used for detecting phosphorus based chemical agents, hydrolysis products and pesticides in all weaponized forms. The combination of a MIPs device (e.g., MIPs wells 14 or MIPs sensor 15) with the denuder 10, as described in the embodiments herein, provides a practical answer to a problem that has plagued the industry.

Figure 4:
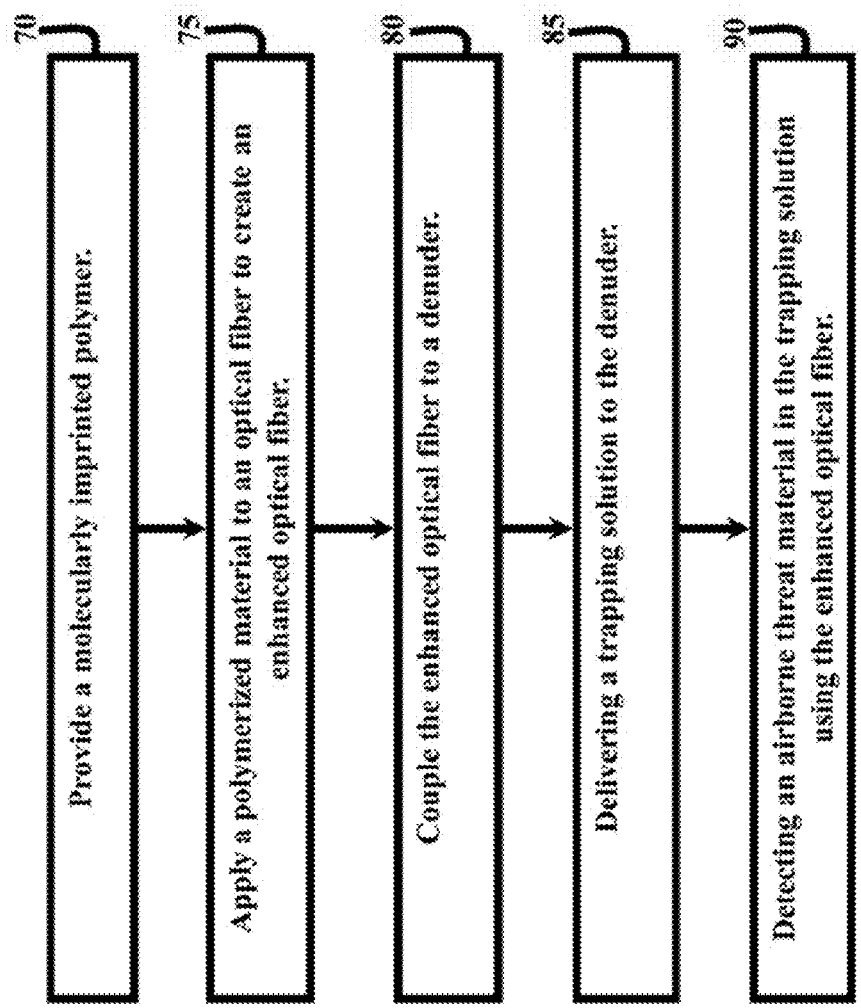
FIG. 4 illustrates a flow diagram of a method of detecting gases, aerosols, and solutions according to an embodiment herein.

FIG. 4 illustrates a flow diagram of a method of detecting gases, aerosols, liquids and/or vapors according to an embodiment herein. As described above, MIPs are synthesized by first preparing complexes of the target using a stoichiometric ratio of europium, target and vinyl substituted monomer. In the embodiment described below, the number of binding species is chosen to accommodate the nine coordinate Eu (III). Step 70, in the method shown in FIG. 4, provides a molecularly imprinted polymer. While not shown in FIG. 4, in one embodiment, the europium nitrate ($Eu(NO_3)_3$) is prepared by dissolving europium oxide in water with sufficient nitric acid to produce a clear solution. A calculated amount of each organophosphonate is diluted and dissolved in an approximately 50/50 water-methanol mixture to which the vinyl monomer is subsequently added. The resulting solution is subsequently added to the $Eu(NO_3)_3$ solution and the pH adjusted with sodium hydroxide to an approximate pH of 9-10 for complexation. The resulting solutions are then stirred on low heat for approximately 4 hours, then covered with a watch glass and left to crystallize overnight. The crystals are then filtered, dried and the spectra interpreted to determine the symmetry changes associated with analyte inclusion.

Once the complexes are made according, for example, to the process described above, step 75 applies a polymerized material to an optical fiber to create an enhanced optical fiber. For example, in one embodiment herein, polymeric coatings are prepared by dissolving approximately 1-5 mole percent complex compound in styrene with approximately 0.1 mole percent azobis(isobutyronitrile) (AIBN) added as an initiator, and 1-5 mole percent divinyl benzene (DVB) added as a cross-linking agent. The resulting solutions are placed in glass vials, purged with nitrogen, and sealed using parafilm and screw on tops. Upon sonication, the partially polymerized material is directly dip coated on to the tapered end of specially prepared optical fibers. According to one embodiment herein, these fibers range from approximately 200-1000 microns and are SMA terminated at one end and tapered at the other end to allow for better light collection into the fiber. Thereafter, the polymer-coated fibers (or substrates) are cured under a small UV lamp for approximately 2 hours. Once cured, the polymers are then swelled in water with gradually increasing amounts of methanol to remove any remaining unreacted monomer and expand the polymer pores to produce accessible sites and facilitate the removal of the imprinting molecules. The imprinted molecules are then removed by washing with approximately 1.0 M nitric acid, leaving a weakly coordinated nitrate ion.

In step 80 of the method shown in FIG. 4, the enhanced optical fiber prepared in step 75 is coupled to a denuder (e.g., denuder 10 shown in FIG. 2). Thereafter, in step 85, a trapping solution (e.g., trapping solution 35 shown in FIG. 2) is delivered (e.g., delivery device 20 shown in FIG. 2) to the denuder (e.g., denuder 10 shown in FIG. 2). For example, according to one embodiment herein, the trapping solution is delivered to the denuder at a rate between 1-4 mL/min using a chemical pump, i.e. a solenoid, syringe, peristaltic, rotary or HPLC pump. Step 90, of the method shown in FIG. 4, detects an airborne threat material (e.g., threat material 25 shown in FIG. 2) in the trapping solution (e.g., trapping solution 35 shown in FIG. 2) using the enhanced optical fiber (e.g., as prepared in step 75). For example, according to one embodiment herein, detection is based on luminescence of the molecularly imprinted polymer excited at 354 nm or 465.8 nm using a solid state, ion, or diode laser, or an LED (e.g., excitation source 50 shown in FIG. 2). The resulting spectra are then collected using a miniature fiber optic spectrometer (e.g., spectrometer 55 shown in FIG. 2) or with a monochromator with a direct fiber coupler and CCD camera. The intensity of the light emitted in the 600-700 nm range of the spectra is directly proportional to the amount of threat material (e.g., threat material 25 shown in FIG. 2) present.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for sensing an air or solution borne threat material within a sample of ambient air or solution, said system comprising:
    a trapping solution;
    a delivery device transporting said trapping solution;
    a denuder fluidically connected to said delivery device to receive said trapping solution and be in contact with said trapping solution and contacting ambient air, wherein said denuder infuses said sample into said trapping solution;
    a molecularly imprinted polymer (MIP) sensor disposed within a collection container and operatively connected to said denuder, wherein said MIP sensor captures and detects said threat material in said sample infused into said trapping solution;
    an excitation source operatively connected to said MIP sensor and having an excitation band, wherein said excitation band excites said threat material providing unique emission band(s); and
    an analytical device operatively connected to said MIP sensor, wherein said analytical device senses the presence of said threat material in said sample.

2. The system of claim 1, wherein said excitation source comprises any of an ion laser, diode laser, solid state laser, tunable laser, pen light and light emitting diode.

3. The system of claim 1, wherein said MIP sensor comprises at least one of an optical fiber, a well plate, a mirror, a cuvette, and any other substrate/platform having disposed thereon a molecularly imprinted polymer chemically binding to said threat material.

4. The system of claim 3, wherein said molecularly imprinted polymer includes a lanthanide-complex comprising a lanthanide ion derived from a lanthanide comprising any of lanthanum, cerium, praseodymium, neodymium, promethium, samarium, europium, gadolinium, terbium, dysprosium, holmium, erbium, thulium, ytterbium, and lutetium.

5. The system of claim 4, wherein said lanthanide ion comprises any of a europium ion and a terbium ion.

6. The system of claim 5, wherein said lanthanide ion comprises a +3 europium ion.

7. The system of claim 5, wherein said lanthanide ion is chelated with a polymerized derivate of one or more ligands comprising any of 4-vinyl benzoic acid, methyl-3,5-divinyl benzoate, 4-vinyl-2-hydroxybenzaldehyde oxime, 2-hydroxy-1,2-di-4-vinylphenylethanone or other vinyl substituted ligand.

8. The system of claim 1, wherein said analytical device comprises any of a spectrophotometer, spectrometer, photomultiplier tube, monochromator equipped with a charge-coupled device (CCD) camera, filters, the naked eye, a computing device, and combinations thereof.

9. The system of claim 1, further comprising:
    at least one of a stream selector valve, a series of on/off solution valves and switches, and a solenoid valve operatively connected to said delivery device; and
    at least one standard solution, wherein said standard solution and said trapping solution are operatively transported through at least one of said stream selector valve, said series of on/off solution valves and switches, and said solenoid to said delivery device.

10. The system of claim 1, further comprising:
    a liquid waste container operatively connected to said collection container.

11. The system of claim 10, further comprising:
    an airflow control device operatively connected to said liquid waste container; and
    a vacuum source operatively connected to said airflow control device.

12. The system of claim 11, wherein said airflow control device comprises at least one of a mass flow controller, limiting orifice, and a rotometer.

13. The system of claim 1, wherein said threat material comprises at least one of a liquid, gas, and aerosol of at least one of an organophosphorus and other target chemical of interest.

14. The system of claim 1, wherein said delivery device comprises at least one of a solenoid, syringe, peristaltic, rotary, high performance liquid chromatography (HPLC) and other liquid pump.

* * * * *